United States Patent
Höland et al.

(10) Patent No.: US 7,846,857 B2
(45) Date of Patent: Dec. 7, 2010

(54) DENTAL GLASS CERAMICS

(75) Inventors: Wolfram Höland, Schaan (LI); Christian Ritzberger, Nenzing (AT); Volker Rheinberger, Vaduz (LI); Elke Apel, Sevelen (CH)

(73) Assignee: Ivoclar Vivadent AG, Schaan (LI)

( * ) Notice: Subject to any disclaimer, the term of this patent is extended or adjusted under 35 U.S.C. 154(b) by 102 days.

(21) Appl. No.: 11/921,816

(22) PCT Filed: May 31, 2006

(86) PCT No.: PCT/EP2006/062761

§ 371 (c)(1), (2), (4) Date: Aug. 29, 2008

(87) PCT Pub. No.: WO2006/131473

PCT Pub. Date: Dec. 14, 2006

(65) Prior Publication Data

US 2009/0023574 A1    Jan. 22, 2009

(30) Foreign Application Priority Data

Jun. 8, 2005   (DE) ................ 10 2005 026 269

(51) Int. Cl.
*C03C 10/02*   (2006.01)

(52) U.S. Cl. ............... 501/10; 106/35; 65/33.1; 65/33.6; 65/33.9

(58) Field of Classification Search .............. 501/10; 106/35; 65/33.1, 33.6, 33.9
See application file for complete search history.

(56) References Cited

U.S. PATENT DOCUMENTS

| | | | |
|---|---|---|---|
| 4,314,909 A * | 2/1982 | Beall et al. ........... | 588/11 |
| 5,948,516 A | 9/1999 | Kriven et al. | |
| 6,121,175 A * | 9/2000 | Drescher et al. ....... | 501/59 |
| 7,291,571 B2 * | 11/2007 | Sprenger et al. ....... | 501/9 |
| 7,300,896 B2 * | 11/2007 | Zachau et al. ......... | 501/9 |

FOREIGN PATENT DOCUMENTS

| | | |
|---|---|---|
| DE | 44 23 794 | 2/1996 |
| DE | 197 25 552 | 12/1998 |
| DE | 102 45 234 | 4/2004 |
| DE | 103 51 885 | 5/2004 |
| DE | 103 46 197 | 4/2005 |
| EP | 0 043 643 | 1/1982 |

* cited by examiner

*Primary Examiner*—Karl E Group
(74) *Attorney, Agent, or Firm*—Lucas & Mercanti, LLP; Klaus P. Stoffel

(57) ABSTRACT

The invention relates to dental glass-ceramics and a process for producing them and their use, with these comprising at least one crystal phase containing xenotime or monazite or mixtures thereof.

15 Claims, No Drawings

DENTAL GLASS CERAMICS

The invention relates to dental glass-ceramics and a process for producing them and their use.

It is known from the prior art that glass-ceramics for industrial applications and for dental glass-ceramics are characterized by a microstructure which comprises one or more crystal phases or one or more glass phases. It should be said at the beginning that a known method of producing such a microstructure is controlled crystallization of starting glasses by control of the nucleation and crystallization processes in the specific starting glass. On this basis, there are many complicated systems which serve as starting glasses for dental glass-ceramics (W. Höland, G. H. Beall, Glass-ceramic technology 2002, The American Ceramic Society, Westerville, Ohio, USA). The optical properties are of particular significance in dental glass-ceramics. The excellent property of precious stones and jewels is likewise their optical brilliance. The prior art in which minerals having the character of precious stones or jewels are known in glass-ceramics will therefore be analyzed first. The above-cited reference (Höland, Beall, 2002) discloses, for example, glass-ceramics which comprise crystals of the spinel, enstatite or cordierite type for industrial applications. These crystal types are, for example, known as precious stones or jewels. However, the optical properties do not play a role in these glass-ceramics for industrial applications.

Natural hydroxyapatite, $Ca_5(PO_4)_3OH$, is also known as a jewel. Owing to the relatively high OH content of natural apatite, this crystal could not be formed in dental glass-ceramics for restorative dental medicine. For this reason, fluoroapatite, $Ca_5(PO_4)_3F$, has been developed by a synthetic route in glass-ceramics for the restoration of teeth.

The xenotime crystal, $YPO_4$, also has jewel character. Products comprising xenotime crystals are known from the prior art (J. Am. Ceram. Soc. 81, 1998, 2216-2218). Such products are used, for example, in medicine for the treatment of tumors (Kawashita et al. Biomaterials 24(2003) Number 17, 2955 to 2963). Use in technology as ceramic composite is known from U.S. Pat. No. 5,948,516.

DE 102 45 234 A1 describes xenotime-containing glass-ceramics as products having a high elastic modulus. These products are glass-ceramics which are low in $SiO_2$ and rich in $Al_2O_3$ for industrial applications. This prior art says nothing about the optical properties. A similar situation applies to DE 103 46 197 A1.

It is an object of the present invention to provide a dental glass-ceramic which has improved optical properties compared to the prior art and can be used, in particular, for materials for restorative dentistry. The objective is to achieve light transmission (translucency), light scattering and diffraction which correspond to those of natural teeth. Furthermore, dental glass-ceramics which can be used as special components for facing materials having good optical aesthetics are to be provided. Here, it should be made possible to provide facings.

This object is achieved by the dental glass-ceramic comprising, as main crystal phase, precious stones and/or jewels, preferably crystals of the xenotime type or monazite type or mixtures thereof or comprising their mixed crystals or related crystals, e.g. those of the rhabdophane type.

In the glass-ceramics of the invention, preference is given to xenotime and/or monazite crystals or crystals of the xenotime and/or monazite types, e.g. $YPO_4$, $ErPO_4$, $YbPO_4$, $LuPO_4$, $LaPO_4$, $CePO_4$, $DyPO_4$, $GdPO_4$ or $TbPO_4$, being formed. It is likewise possible to use their mineralogical relatives such as those of the rhabdophane and/or weinschenkite type, e.g. $RPO_4*(0.5-1)Z$ or $RPO4*2Z$, where R is a rare earth element, e.g. Y, Er or Dy, and Z is preferably $H_2O$ in minerals.

In the glass-ceramics of the invention, the formation of xenotime or related phases is preferred. This means that, according to the invention, the main crystal phase comprises $YPO_4$ or consists of this compound. It is likewise possible for mixtures of one or more of the abovementioned further crystals of the xenotime type, monazite type, their mixed crystals or related crystals, e.g. those of the rhabdophane type, to be formed according to the invention. Further details regarding xenotimes and monazites may be found, for example, in the following references:

Ushakov, S. V., Helean, K. B. and Navrotsky, A. "Thermochemistry of rare-earth orthophosphates", Journal Mater. Res., Vol. 16, No. 9, 2623-2632 (September 2001), Inoue, M. Nakamura, T., Otsu, H., Kominami, H. and Inui T. Nippon Kagaku Kaishi 5, 612 (1993), Hikichi, V., Yu, C. F., Miyamoto, V. and Okada, S. J. Alloys Compd. 192, 102 (1993) Hikichi et al., J. Am. Ceram. Soc. 76, 1073-1076 (1989).

The main crystal phase can be produced by controlled volume nucleation and crystallization in the starting glass, so that the crystals grow individually and distributed randomly through the volume and their size can be controlled in the range from 0.1 to 10 µm, preferably from 0.1 to 2 µm.

The control of the crystal growth processes is brought about by means of two main effects: the choice of the composition and the subsequent heat treatment of the molten starting glasses. Here, both the temperature and the time play important roles. A particular aspect of the heat treatment is that not only single-stage but also multistage thermal treatments lead to crystallization. A special case is a glass melt which is supersaturated with ions and groups for the crystals so that it forms crystals immediately on cooling, i.e. without an additional heat treatment. This crystallization proceeds spontaneously, i.e. not in a controlled fashion, so that the crystal size is not controllable here. Control is only possible by means of an additional thermal treatment.

According to the invention, further secondary crystal phases can be present in the dental glass-ceramic in addition to the main xenotime crystal phase. Possible secondary crystal phases of this type are, proceeding from the composition of the starting glasses, apatite or leucite in particular. According to the invention, it is surprising that the advantageous properties, in particular the optical properties such as translucence with controllable opalescence and thermal properties such as variable sintering temperatures, which are determined by the main crystal phase composed of xenotime crystals are also maintained in a mixed glass-ceramic microstructure containing the secondary crystal phases described.

Furthermore, the mixed crystal ceramics described are compatible with other dental glass-ceramics, e.g. leucite dental glass-ceramics or leucite-apatite dental glass-ceramics. Further possible applications of the dental glass-ceramic of the invention for producing sintered glass-ceramics comprising leucite and/or leucite-apatite glass-ceramic systems are thus opened up.

According to the invention, the further glasses are preferably selected from the group consisting of opal glasses, alkali metal silicate glasses and/or potassium-zinc silicate glasses which sinter at a low temperature and the further glass-ceramics are preferably selected from the group consisting of low-sintering apatite glass-ceramics, translucent apatite glass-ceramics, sinterable lithium silicate glass-ceramics, $ZrO_2$—$SiO_2$ glass-ceramics and/or leucite-containing phosphosilicate glass-ceramics.

The xenotime type glass-ceramics according to the invention can be mixed with other glasses and/or glass-ceramics. In this case, the xenotime glass-ceramic forms the main component in a, for example inorganic, composite. The glass-ceramics of the invention can here be combined with many other glass-ceramics in order to set particular optical, mechanical or thermal properties. Examples of such glasses or glass-ceramics may be found, for example, in DE 43 14 817 A1, DE 44 23 793 A1, DE 44 23 794 A1, DE 44 28 839 A1, DE 196 47 739 A1, DE 197 25 552 A1 and DE 100 31 431 A1. Such glasses and glass-ceramics are preferably derived from silicates, borates or phosphates or aluminate-silicate systems. Preferred glass-ceramics are derived from the following systems: $SiO_2$—$Al_2O_3$—$K_2O$ having cubic or tetragonal leucite crystals, $SiO_2$—$B_2O_3$—$Na_2O$, alkali metal silicates, alkali metal-zinc silicates, silicophosphate systems and/or the $SiO_2$—$ZrO_2$ base system. In the mixing of such glasses and/or glass-ceramics with xenotime glass-ceramics according to the invention, the thermal expansion coefficient of the resulting mixed glass-ceramics can be set in the range from 7 to $20*10^{-6}K^{-1}$, measured in the range from 100 to 400° C.

Furthermore, the dental glass-ceramic of the invention can additionally contain one or more color-imparting or fluorescence-producing metal oxides. Preference is here given to metals of transition groups 1 to 8 including the rare earth elements of the Periodic Table of the Elements.

The dental glass-ceramic of the invention comprises, as main components, $SiO_2$, $Al_2O_3$, $Y_2O_3$ and $P_2O_5$. As additional components, it is possible to use, for example, $Na_2O$, $K_2O$, $B_2O_3$, $Li_2O$, $ZrO_2$, $CeO_2$, $TiO_2$, $ZnO$, $CaO$, $La_2O_3$, $Tb_4O_7$ or fluoride. According to the invention, preference is given to alkali metal oxides, in particular $Na_2O$ or $K_2O$.

A possible general composition of the dental glass-ceramic of the invention having xenotime and/or monazite crystals and/or crystals of the xenotime or monazite type is, for example, the following:

| Component | % by mass |
|---|---|
| $SiO_2$ | 40-65 |
| $Al_2O_3$ | 5-25 |
| R oxides | 0.5-30 |
| $P_2O_5$ | 0.5-10 | where the R oxides are selected from the group consisting of $Y_2O_3$, $CeO_2$, $La_2O_3$, $Tb_4O_7$, $Er_2O_3$ and/or $Lu_2O_3$.

Thus, a preferred dental glass-ceramic according to the invention comprises

| Component | % by mass |
|---|---|
| $SiO_2$ | 45-60 |
| $Al_2O_3$ | 8-20 |
| $Y_2O_3$ | 5-30 |
| $P_2O_5$ | 1-10 |
| $B_2O_3$ | 0-10 |
| $Na_2O$ | 0-15 |
| $K_2O$ | 0-15 |
| $Li_2O$ | 0-5 |
| $CaO$ | 0-10 |
| fluoride | 0-5 |

The sum of the components present in the glass or the glass-ceramic is always 100% by mass.

Furthermore, it has been found that the molar ratio of $P_2O_5$ to $Y_2O_3$ should preferably be in the range from 1:0.5 to 1:3.5. Table 1 below gives the molar ratios for the compositions 1 to 6 in table 2.

TABLE 1

| Chemical component/property | Molar ratios of $P_2O_5:Y_2O_3$ | | | | | |
|---|---|---|---|---|---|---|
| | 1 | 2 | 3 | 4 | 5 | 6 |
| $P_2O_5$ | 1.0 | 1.0 | 1.0 | 1.0 | 1.0 | 1.0 |
| $Y_2O_3$ | 1.0 | 1.58 | 3.15 | 1.58 | 1.59 | 2.0 |
| Crystal phase | $YPO_4$•* 0.8 Z | $YPO_4$• 0.8 Z and fluoro-apatite | $YPO_4$* 0.8 Z | $YPO_4$* 0.8 Z | $YPO_4$•* 0.8 Z | $YPO_4$ |

While Z in minerals is preferably $H_2O$, in synthetic glasses and glass-ceramics it represents foreign ions or lattice defects.

The novel dental glass-ceramics described in the various compositions have excellent translucent properties with a controlled contrast ratio, without a completely white, opaque body without any translucence (corresponds to a contrast ratio of 1.0) being formed. The contrast ratio, measured in accordance with the Dental Standard BS 5612, should be less than or equal to 0.8 and is preferably in the range from 0.40 to 0.78.

Furthermore, the dental glass-ceramics have good processing properties. Since they can also be mixed with further glass-ceramics, they are preferably used in restorative dentistry, in particular as sinterable facing material.

The good chemical resistance of the dental glass-ceramics of the invention is also advantageous. They have, in particular, an excellent acid resistance which preferably corresponds to a loss in mass of less than 100 µg/cm$^2$.

The dental glass-ceramics of the invention can be produced by customary methods known from the prior art. For example, the process of DE 197 50 794 A1 can be used for the dental glass-ceramics of the invention. Here, a melt of the starting glass is shaped in the desired way and cooled. The shaped glass product is subjected to a heat treatment to give a glass-ceramic product shaped as a blank. This production process gives monolithic bodies.

In a variant of the invention, the glass-ceramic can be produced by the so-called massive glass/glass-ceramic technique:

In step (a), a melt of a starting glass containing the components of the glass-ceramic is produced. For this purpose, a corresponding mixture of suitable starting materials, e.g. carbonates, oxides, fluorides and phosphates, is prepared and heated to temperatures of preferably from 1300 to 1600° C. for from 2 to 10 hours. To obtain a particularly high degree of homogeneity, the glass melt obtained can be poured into water to form glass granules and the glass granules obtained can be melted again.

In step (b), the melt of the starting glass is poured into an appropriate mold, e.g. a steel mold, and cooled to room temperature to obtain a glass product, e.g. a glass blank.

In the third process step (c), the glass blank is subjected to a single-stage or multistage thermal treatment in the temperature range from 700° C. to 1200° C. for a period of from 30 minutes to about 6 hours in order to bring about nucleation and crystallization. Temperatures in the range from 700° C. to about 1000° C. and times ranging from one to four hours are preferred for these thermal treatments.

Cooling is preferably carried out in a controlled manner in order to allow relaxation of the glass and avoid stresses in the structure associated with rapid temperature changes. In general, the melt is therefore poured into molds preheated to, for example, 400° C. The glass blank can subsequently be cooled slowly to room temperature in an oven.

In a further variant of the invention, powders can be produced. Thus, the xenotime-type glass-ceramic of the invention can be produced by the following procedure:

a) processing of a homogeneous raw material mix comprising the required components at temperatures of from 1200° C. to 1650° C. to form a glass melt,
b) fritting of the resulting glass melt by introduction into a water bath to form glass granules,
c) comminution of the glass granules, if appropriate, to give a glass powder having an average particle size of from 1 to 500 μm, based on the number of particles, and
d) subsequent thermal treatment (single-stage or multistage) of the glass granules or glass powder at from 700 to 1200° C. for a period of from 30 minutes to 6 hours.

In step a), the individual components required, e.g. carbonates, oxides, fluorides and phosphates, are firstly homogeneously mixed with one another and heated to the temperatures indicated. This forms the desired starting glass.

In step b), the glass melt obtained is subsequently quenched by pouring into water. This forms glass granules. This production step is usually referred to as fritting.

If appropriate, the glass granules are after-comminuted in step c) and milled to a preferred particle size, mainly using conventional mills. The glass powder produced in this way then has a desired average particle size of from 1 to 500 μm, based on the number of particles.

In step d), the glass granules or, if appropriate, the glass powder are/is then subjected to a thermal treatment at temperatures of from 700 to 1200° C. (single-stage or multistage) for a period of from 30 minutes to 6 hours, preferably from 30 minutes to 3 hours.

The crystals produced in the sintering step d) have a comparatively small size of from about 0.1 to a maximum of 10 μm, preferably from 0.1 to about 2 μm. The crystals are randomly distributed in the glass-ceramic and no points of preferential crystal growth are observed.

The process described makes it possible to obtain blanks, for example for pressing, or powders for sintering to produce a microstructurally composite material.

According to the invention, it is likewise possible to process the dental glass-ceramic in powder form together with further dental glass-ceramic powders. Possible dental glass-ceramics of this type are, for example, leucite or leucite-fluoroapatite. In this way, a dental mixed glass-ceramic is obtained in the end product.

This mode of operation very clearly shows up the advantages of the dental glass-ceramic of the invention which manifest themselves especially in the excellent processing properties of the xenotime-containing dental glass powder. These advantages can be seen, in particular, in the sinterability in a wide temperature range while maintaining the optical properties.

The dental glass-ceramics of the invention can be used in the above-described way for, in particular, producing mixed glass-ceramics, in particular as sinterable facing material for metal or ceramic substrates.

According to the invention, it is possible to produce glass blanks or glass-ceramic blanks which are pressed by means of a glass-ceramic pressing technique (e.g. Empress® technology from Ivoclar Vivadent AG) to produce a vitreous or ceramic shaped body for use in dental restoration. Likewise, the monolithic body can be machined (e.g. CAD/CAM process) to produce a shaped body for use in dental restoration.

The dental glass-ceramics of the invention can also be used as opacifying component, dental material or any dental restorations. The dental material can be used as coating material or facing material. The dental restorations can be a crown, a bridge, a part crown, an onlay, an inlay, an artificial tooth, a stump buildup or a facing. The coating material can be used for coating metal and/or ceramic substrates.

The invention is illustrated below with reference to the examples:

TABLE 2

Compositions and crystal phases of glass-ceramics according to the invention
Concentration in % by mass

| Chemical component/property | 1 | 2 | 3 | 4 | 5 | 6 |
|---|---|---|---|---|---|---|
| $SiO_2$ | 58.3 | 47.4 | 50.5 | 48.0 | 48.1 | 45.8 |
| $Al_2O_3$ | 16.6 | 10.6 | 8.3 | 8.1 | 8.2 | 19.2 |
| $Y_2O_3$ | 2.2 | 9.4 | 18.8 | 18.4 | 18.5 | 26.7 |
| $B_2O_3$ | 0.3 | 7.9 | | | | |
| $Na_2O$ | 6.4 | 7.1 | 8.3 | 8.1 | 8.2 | |
| $K_2O$ | 9.9 | 10.9 | 7.2 | 7.0 | 7.1 | |
| $Li_2O$ | | | 1.00 | 1.0 | 1.0 | |
| CaO | | 2.3 | | | | |
| ZnO | 1.2 | | | | | |
| $P_2O_5$ | 1.2 | 3.7 | 3.7 | 7.3 | 7.4 | 8.3 |
| $TiO_2$ | 1.1 | | | | | |
| $ZrO_2$ | 2.2 | | 0.8 | 0.8 | 0.8 | |
| F | 0.6 | 0.7 | 0.7 | 0.6 | | |
| $CeO_2$ | | | 0.7 | 0.7 | 0.7 | |
| Melting conditions | 1650° C./ 2 h | 1550° C./ 1 h | 1550° C./ 1.5 h | 1550° C./ 1.5 h | 1550° C./ 1.5 h | 1600° C./ 1 h |
| Type of sample | powder | powder | powder | powder | powder | monolith |

TABLE 2-continued

Compositions and crystal phases of glass-ceramics according to the invention
Concentration in % by mass

| T/t (° C., h) | 8 h/950° C. | 800/1 + 1050/0.5 | 1050/1 | 850/2 | 1050/1 | none |
|---|---|---|---|---|---|---|
| Crystal phases | $YPO_4*0.8\ Z$ | $YPO_4*0.8\ Z$ and F-apatite | $YPO_4*•0.8\ Z$ | $YPO_4*•0.8\ Z$ | $YPO_4•*0.8\ Z$ | $YPO_4$ (xenotime) |

| Chemical component/property | 7 | 8 | 9 | 10 |
|---|---|---|---|---|
| $SiO_2$ | 56.8 | 57.8 | 55.0 | 48.1 |
| $Al_2O_3$ | 9.3 | 9.5 | 9.0 | 13.2 |
| $Y_2O_3$ | 6.0 | 6.2 | 12.3 | 5.6 |
| $B_2O_3$ | — | — | — | 7.2 |
| $Na_2O$ | 9.3 | 9.5 | 9.1 | 4.4 |
| $K_2O$ | 8.0 | 8.2 | 7.8 | 11.1 |
| $Li_2O$ | 1.1 | 1.1 | 1.1 | — |
| CaO | 3.7 | 3.8 | — | — |
| ZnO | — | — | — | — |
| $P_2O_5$ | 4.1 | 2.1 | 4.0 | 7.0 |
| $TiO_2$ | — | — | — | 1.1 |
| $ZrO_2$ | 0.9 | 1.0 | 0.9 | 1.7 |
| F | — | — | — | 0.6 |
| $CeO_2$ | 0.8 | 0.8 | 0.8 | — |
| Melting conditions | 1550° C./1/5 h | 1550° C./1.5 h | 1550° C./1.5 h | 1650° C./1 h |
| Type of sample | powder | powder | powder | powder |
| T/t (° C., h) | | | 1000/40 | 850/1 |
| Crystal phases | | | $Na_{3.6}Y_{1.8}(PO_4)_3$ | $YPO_4*0.8\ Z$ |

| Chemical component/property | 11 | 12 | 13 | 14 |
|---|---|---|---|---|
| $SiO_2$ | 41.7 | 46.7 | 56.0 | 49.5 |
| $Al_2O_3$ | 9.3 | 9.7 | 15.9 | 13.5 |
| $Y_2O_3$ | 8.3 | — | — | 5.7 |
| $La_2O_3$ | 12.0 | 12.5 | — | — |
| $Tb_4O_7$ | — | — | 6.2 | — |
| $B_2O_3$ | 7.0 | 3.2 | 0.3 | 7.5 |
| $Na_2O$ | — | 2.8 | 6.2 | 4.6 |
| $K_2O$ | 9.6 | 6.0 | 9.4 | 11.7 |
| $Li_2O$ | — | 1.5 | — | — |
| CaO | — | 2.9 | — | — |
| ZnO | — | — | 1.1 | — |
| $P_2O_5$ | 5.2 | 5.4 | 1.2 | 7.1 |
| $TiO_2$ | — | — | 1.0 | — |
| $ZrO_2$ | — | — | 2.1 | — |
| F | 0.6 | 0.6 | 0.6 | 0.6 |
| Melting conditions | 1550° C./1.5 h | 1550° C./1.5 h | 1650° C./2 h | 1550° C./1.5 h |
| Type of sample | powder | powder | powder | powder |
| T/t (° C., h) | 800/1 + 1050/0.5 | 800/1 + 1050/0.5 | 950/8 | 850° C./1 |
| Crystal phases | $LaPO_4$ | $LaPO_4$, $NaY_9(SiO_4)_6O_2$ | $TbPO_4$ | $YPO_4*0.8\ Z$ |

Notes:

Examples 1-5 represent xenotime-type glass-ceramics.

Example 6 represents xenotime, the glass is supersaturated and crystallization occurs spontaneously on cooling the melt.

In examples 1-5, the main crystal phase formed is a xenotime type of the formula $YPO_4*0.8\ Z$. This crystal phase was confirmed on the basis of the JCPDS-42-0082 reference (JACTAW, volume 72, page 1073, (1989) primary reference: Hikichi, Y., Sasaki, T., Murayama, K., Nomura, T., Miyamoto, M.). This crystal phase appeared as per this reference as hydrate phase $YPO_4•0.8\ H_2O$ and could also be designated as a rhabdophane type according to Hikichi et al. (1989). Since the glass-ceramics of the invention are high-temperature products, it can be assumed that such a high water content will not be present in the starting glass of the glass-ceramics but other ions will have been incorporated instead. Fluoride or oxygen or other ions which are known among the isotypes of apatite or else lattice defects are conceivable here. This is shown in example 5, since this crystal type is also formed without fluoride so that other foreign ions were incorporated into this crystal lattice.

In example 2, fluoroapatite was formed as secondary phase.

Example 9 demonstrates the glass-ceramic having xenotime-type crystals which have incorporated Na$^+$ ions into the crystal structure and corresponds to the formula Na$_{3.6}$Y$_{1.8}$(PO$_4$)$_3$.

Examples 11 to 13 demonstrate glass-ceramics having monazite-type crystals LaPO$_4$ and TbPO$_4$, with a secondary phase of the NaY$_9$(SiO$_4$)$_6$O$_2$ type additionally being detected in example 12.

The following table shows some of the properties of selected compositions.

TABLE 3

Properties of selected glass-ceramics

| Property/ glass-ceramic as per table 1 | 2 | 9 | 11 | 14 |
|---|---|---|---|---|
| Sintering temperature (° C.) | 840 | 960 | 940 | 940 |
| CTE$_{100-400}$ (K$^{-1}$) | 9.6 * 10$^{-6}$ | 10.6 * 10$^{-6}$ | 9.5 * 10$^{-6}$ | — |
| Chemical resistance (µg/cm$^2$) | 73 | 27.5 | 33.8 | — |
| Appearance | n.d. | milky | milky opaque | milky |
| CR | n.d. | 68.15 | 99.67 | 55.05 |
| L | n.d. | 85.42 | 92.63 | 76.06 |
| a | n.d. | −0.89 | −0.16 | −0.26 |
| b | n.d. | 1.73 | 1.36 | −0.89 |

The letters CR, L, a and b have the following meanings:
CR contrast ratio (=degree of opacity)
L luminance
a color saturation on the red-green axis
b color saturation on the blue-yellow axis

The invention claimed is:

1. A process for using a glass-ceramic as a dental glass-ceramic, comprising providing the glass-ceramic with at least one crystal phase containing xenotime or monazite or mixtures thereof, and using the glass-ceramic in a dental application.

2. The process according to claim 1, wherein the glass-ceramic contains crystals having a size of from 0.1 µm to 10 µm.

3. The process according to claim 1, wherein the glass-ceramic contains at least SiO$_2$, Al$_2$O$_3$, R oxides and P$_2$O$_5$, where R is a rare earth.

4. The process according to claim 3, wherein the R oxides are selected from the group consisting of Y$_2$O$_3$, Er$_2$O$_3$, Lu$_2$O$_3$, La$_2$O$_3$, CeO$_2$ and Tb$_4$O$_7$.

5. The process according to claim 3, wherein the glass-ceramic has a composition of components comprising

| | |
|---|---|
| SiO$_2$ | 40-65% by mass |
| Al$_2$O$_3$ | 5-25% by mass |
| R oxides | 0.5-30% by mass |
| P$_2$O$_5$ | 0.5-10% by mass |
| fluoride | 0-5% by mass |
| additional oxides | 5-30% by mass | and the sum of the components is 100% by mass.

6. The process according to claim 5, wherein one or more additional oxides are selected from the group consisting of Li$_2$O, Na$_2$O, K$_2$O, CaO, MgO, ZnO, B$_2$O$_3$, TiO$_2$ and ZrO$_2$.

7. The process according to claim 1, wherein the glass-ceramic is composed of

| | |
|---|---|
| SiO$_2$ | 45-60% by mass |
| Al$_2$O$_3$ | 8-20% by mass |
| Y$_2$O$_3$ | 5-30% by mass |
| P$_2$O$_5$ | 1-10% by mass |
| B$_2$O$_3$ | 0-10% by mass |
| Na$_2$O | 0-15% by mass |
| K$_2$O | 0-15% by mass |
| Li$_2$O | 0-5% by mass |
| CaO | 0-10% by mass |
| fluoride | 0-5% by mass |
| further oxides | 0-10% by mass | and the sum of the components is always 100% by mass.

8. A process for producing a dental glass-ceramic comprising at least one crystal phase containing xenotime or monazite or mixtures thereof wherein
   (a) the components required for producing the glass-ceramic are mixed and melted to form a glass,
   (b) the glass melt from step (a) is converted by fritting into glass granules,
   (c) optionally the glass granules are comminuted to give a powder having an average particle size of from 1 to 500 µm (based on the number of particles) and
   (d) the glass granules from step (b) or the glass powder from step (c) are/is subsequently subjected to a single-stage or multistage thermal treatment in the temperature range from 700° C. to 1200° C. for a period of from about 30 minutes to about 6 hours.

9. The process according to claim 8, further including using the glass-ceramic as an opacifying agent, dental material for producing a dental material or a dental restoration.

10. A dental glass-ceramic comprising at least one crystal phase containing xenotime or monazite or mixtures thereof, and a composition of

| | |
|---|---|
| SiO$_2$ | 40-65% by mass |
| Al$_2$O$_3$ | 5-25% by mass |
| R oxides | 0.5-30% by mass |
| P$_2$O$_5$ | 0.5-10% by mass |
| fluoride | 0-5% by mass |
| additional oxides | 5-30% by mass | and the sum of the components is 100% by mass,
wherein the R oxides are selected from the group consisting of Y$_2$O$_3$, Er$_2$O$_3$, Lu$_2$O$_3$, La$_2$O$_3$, CeO$_2$ and Tb$_4$O$_7$, and
wherein one or more additional oxides are selected from the group consisting of Li$_2$O, Na$_2$O, K$_2$O, CaO, MgO, ZnO, B$_2$O$_3$, TiO$_2$ and ZrO$_2$.

11. The dental glass-ceramic according to claim 10, wherein the glass-ceramic is composed of

| | |
|---|---|
| SiO$_2$ | 45-60% by mass |
| Al$_2$O$_3$ | 8-20% by mass |
| Y$_2$O$_3$ | 5-30% by mass |
| P$_2$O$_5$ | 1-10% by mass |
| B$_2$O$_3$ | 0-10% by mass |
| Na$_2$O | 0-15% by mass |
| K$_2$O | 0-15% by mass |
| Li$_2$O | 0-5% by mass |
| CaO | 0-10% by mass |
| fluoride | 0-5% by mass |
| further oxides | 0-10% by mass | and the sum of the components is always 100% by mass.

12. A process for producing a dental glass-ceramic according to claim 10, wherein
(a) the components required for producing the glass-ceramic are mixed and melted to form a glass,
(b) the glass melt from step (a) is converted by fritting into glass granules,
(c) optionally the glass granules are comminuted to give a powder having an average particle size of from 1 to 500 µm (based on the number of particles) and
(d) the glass granules from step (b) or the glass powder from step (c) are/is subsequently subjected to a single-stage or multistage thermal treatment in the temperature range from 700° C. to 1200° C. for a period of from about 30 minutes to about 6 hours, or
(a) the components required for producing the glass-ceramic are mixed and melted to form a glass,
(b) the glass melt from step (a) is poured into a pre-heated mold and is cooled in a controlled manner to room temperature in order to obtain a shaped glass blank and
(c) optionally the glass blank is subjected to a single-stage or multistage thermal treatment in the temperature range from 700° C. to 1200° C. for a period of from 30 minutes to about 6 hours.

13. A process for producing a mixed glass-ceramic comprising the step of mixing a pulverulent dental glass-ceramic containing xenotime and/or monazite crystals as claimed in claim 10, with further pulverulent glasses or glass-ceramics.

14. A process for producing a dental material or a dental restoration, including manufacturing the dental material or dental restoration using dental glass-ceramics according to claim 10 as an opacifying component.

15. A process for producing a dental material or a dental restoration, including manufacturing the dental material or dental restoration using the mixed glass-ceramics produced according to claim 13 as an opacifying component.

* * * * *